(12) United States Patent
Moore et al.

(10) Patent No.: US 7,245,964 B2
(45) Date of Patent: Jul. 17, 2007

(54) ANNOTATING AN AUDIO RECORDING DURING A MEDICAL EMERGENCY

(75) Inventors: Mark P. Moore, Redmond, WA (US); John Giaever, Seattle, WA (US)

(73) Assignee: MedTronic Physio-Control Corp., Redmond, WA (US)

( * ) Notice: Subject to any disclaimer, the term of this patent is extended or adjusted under 35 U.S.C. 154(b) by 152 days.

(21) Appl. No.: 10/377,992

(22) Filed: Feb. 28, 2003

(65) Prior Publication Data

US 2004/0172070 A1 Sep. 2, 2004

(51) Int. Cl.
*A61N 1/00* (2006.01)

(52) U.S. Cl. ......................................................... 607/5

(58) Field of Classification Search .................... 705/3; 607/5, 6; 128/899, 903, 904, 920, 923–925; 600/300, 510; 434/262
See application file for complete search history.

(56) References Cited

U.S. PATENT DOCUMENTS

| | | | |
|---|---|---|---|
| 3,920,005 A * | 11/1975 | Gombrich et al. .......... | 600/510 |
| 4,635,639 A | 1/1987 | Hakala et al. | |
| 5,462,051 A * | 10/1995 | Oka et al. ................... | 600/300 |
| 5,549,115 A | 8/1996 | Morgan et al. | |
| 5,549,659 A | 8/1996 | Johansen et al. | |
| 5,593,426 A | 1/1997 | Morgan et al. | |
| 5,594,638 A * | 1/1997 | Iliff ............................... | 705/3 |
| 5,674,252 A | 10/1997 | Morgan et al. | |
| 5,680,864 A | 10/1997 | Morgan et al. | |
| 5,683,423 A | 11/1997 | Post | |
| 5,749,902 A | 5/1998 | Olson et al. | |
| 5,749,913 A | 5/1998 | Cole | |
| 5,782,878 A | 7/1998 | Morgan et al. | |
| 5,785,043 A | 7/1998 | Cyrus et al. | |
| 5,787,155 A | 7/1998 | Luna | |
| 5,836,993 A | 11/1998 | Cole | |
| 5,891,046 A | 4/1999 | Cyrus et al. | |
| 5,891,049 A | 4/1999 | Cyrus et al. | |
| 5,899,866 A | 5/1999 | Cyrus et al. | |
| 5,921,938 A | 7/1999 | Aoyama et al. | |
| 5,951,485 A | 9/1999 | Cyrus et al. | |
| 5,999,493 A | 12/1999 | Olson | |

(Continued)

FOREIGN PATENT DOCUMENTS

| EP | 1 002 555 A2 | 5/2000 |
|---|---|---|
| WO | WO 02/060529 | 8/2002 |

OTHER PUBLICATIONS

International Preliminary Report on Patentability from corresponding PCT Application Serial No. PCT/US2004/005775, mailed May 31, 2005 (12 pages).

*Primary Examiner*—George Manuel
(74) *Attorney, Agent, or Firm*—Mary Yawney Redman (57) ABSTRACT

Techniques for managing recording of audio during a medical emergency are presented. An audio recorder may selectively record audio at selected time during the medical emergency, and generate correlation information to temporally correlate the recorded audio with the medical emergency. The audio recorder may establish receive synchronization information from a medical device used during the medical emergency, and may mark recorded audio according to the synchronization information. A computer may generate a record for the medical emergency that includes recorded audio correlated with medical emergency information generated by the medical device. The computer may correlate the recorded audio with the medical emergency information according the synchronization markings.

72 Claims, 7 Drawing Sheets

U.S. PATENT DOCUMENTS

| | | |
|---|---|---|
| 6,041,257 A | 3/2000 | MacDuff et al. |
| 6,047,207 A | 4/2000 | MacDuff et al. |
| 6,057,758 A | 5/2000 | Dempsey et al. |
| 6,064,909 A | 5/2000 | Barkley et al. |
| 6,141,584 A | 10/2000 | Rockwell et al. |
| 6,150,951 A | 11/2000 | Olejniczak |
| 6,201,992 B1 | 3/2001 | Freeman |
| 6,301,502 B1 | 10/2001 | Owen et al. |
| 6,304,780 B1 | 10/2001 | Owen et al. |
| 6,321,113 B1 | 11/2001 | Parker et al. |
| 6,374,138 B1 | 4/2002 | Owen et al. |
| 6,405,083 B1 | 6/2002 | Rockwell et al. |
| 6,427,083 B1 | 7/2002 | Owen et al. |
| 6,438,417 B1 | 8/2002 | Rockwell et al. |
| 6,493,581 B2 | 12/2002 | Russell |
| 6,594,634 B1 | 7/2003 | Hampton et al. |
| 6,597,948 B1 | 7/2003 | Rockwell et al. |
| 6,668,192 B1 | 12/2003 | Parker et al. |
| 2003/0025602 A1 | 2/2003 | Medema et al. |
| 2003/0036683 A1* | 2/2003 | Kehr et al. .............. 600/300 |
| 2003/0058097 A1 | 3/2003 | Saltzstein et al. |
| 2003/0109904 A1 | 6/2003 | Silver et al. |
| 2004/0072134 A1* | 4/2004 | Takahashi ............... 434/262 |

* cited by examiner

FIG. 8

ANNOTATING AN AUDIO RECORDING DURING A MEDICAL EMERGENCY

TECHNICAL FIELD

The invention relates to management of medical emergency information and, more particularly, to management of audio recording during a medical emergency.

BACKGROUND

Devices used to treat patients during medical emergencies may record medical emergency information. For example, a defibrillator used by paramedics to treat a patient may record an electrocardiogram or a heart rate over time via electrodes or paddles attached to the patient. The defibrillator may also record a capnograph, a plethysmograph, a blood oxygen saturation over time, a blood pressure over time, a pulse rate over time, end tidal carbon dioxide measurements, or measurements of the fraction of carbon dioxide in air inspired or expired via appropriate sensors.

The therapies delivered to the patient, and the times at which therapies were delivered to the patient may also be recorded by the defibrillator. For example, the defibrillator may record the amplitude and other characteristics of defibrillation pulses delivered to the patient, and the times at which defibrillation pulses were delivered to the patient. Based on input provided by the paramedics, the defibrillator may also, for example, record the times at which drugs were delivered to the patient, or the times at which cardiopulmonary resuscitation (CPR) was performed on the patient.

After the medical emergency has ended, those who treated a patient may want or need to generate a report detailing the condition and treatment of the patient. For example, paramedics are generally required by rule or law to generate run reports each time they respond to a medical emergency. The run reports may include scene arrival and departure times, assessment of the patient, patient vital signs, a record of treatments, and the like.

Often, paramedics generate such run reports by reviewing the medical emergency information recorded by a defibrillator. The medical emergency information alone is generally insufficient to generate a run report, and must be supplemented by the paramedics using any handwritten notes they may have been taken during the medical emergency and their memories. Because of the time pressure involved in a medical emergency, any notes taken will likely be incomplete, and the memories of the paramedics may be inaccurate. Further, the notes may actually confuse the paramedics because any times jotted down therein will likely be based on a wristwatch that is not synchronized to the defibrillator clock. Consequently, run reports generated in this manner may be incomplete and inaccurate, which may cause problems if the run report is relied upon for performance evaluation, billing, medical research or legal defense in the case of malpractice allegations.

SUMMARY

In general, the invention is directed to techniques for managing recording of audio during a medical emergency. An audio recorder may selectively record audio at selected times during the medical emergency, and generate correlation information to temporally correlate the recorded audio with the medical emergency.

The audio recorder may receive synchronization information from a medical device used during the medical emergency, and may mark recorded audio according to the synchronization information. The medical device, which generates medical emergency information, may also receive synchronization information from the audio recorder, and mark the medical emergency information according to the synchronization information.

A computer may generate a record for the medical emergency that includes recorded audio correlated with medical emergency information generated by the medical device. The computer may correlate the recorded audio with the medical emergency information according to the synchronization markings. The computer may present the record to a user. A paramedic, for example, may use such a record to generate a run report.

In one embodiment, the invention is directed to a method in which audio is recorded during a medical emergency. Correlation information is generated to temporally correlate the recorded audio with the medical emergency. The recorded audio may be marked to correlate the recorded audio with the medical emergency. Synchronization information may be received from a medical device used during the medical emergency, and the recorded audio may be marked according to the synchronization information.

In another embodiment, the invention is directed to a device. The device includes a microphone to detect sound and a processor coupled to the microphone. The processor records audio detected by the microphone during a medical emergency, and generates correlation information to temporally correlate the recorded audio with the medical emergency. The processor may mark the recorded audio to correlate the recorded audio with the medical emergency. The device may include a receiver to receive information from a medical device used during the medical emergency. The processor may receive synchronization information from the medical device via the receiver, and mark the recorded audio according to the synchronization information. The device may comprise a portable audio recorder.

In another embodiment, the invention is directed to a method in which medical emergency information is received from a medical device used during a medical emergency. Recorded audio obtained by an audio recorder during the medical emergency is correlated with the medical emergency information based on a synchronization scheme established between the medical device and the audio recorder.

In another embodiment, the invention is directed to a device that includes a receiver and a processor. The processor receives information from a medical device used during a medical emergency via the receiver. The processor also correlates recorded audio obtained by an audio recorder during the medical emergency with the medical emergency information based on a synchronization scheme established between the medical device and the audio recorder. The device may comprise at least one of the audio recorder and the medical device, and the medical device may comprise a defibrillator.

In another embodiment, the invention is directed to a computer-readable medium containing instructions that cause a programmable processor to receive medical emergency information from a medical device used during a medical emergency. The instructions may further cause a programmable processor to correlate recorded audio obtained by an audio recorder during the medical emergency with the medical emergency information based on a synchronization scheme established between the medical device and the audio recorder.

In another embodiment, the invention is directed to a method in which synchronization information is provided to an audio recorder. Medical emergency information is generated during a medical emergency, and the medical emergency information is marked according to the synchronization information.

In another embodiment, the invention is directed to a device that includes a transmitter to provide information to an audio recorder and a processor. The processor provides synchronization information to the audio recorder via the transmitter. The processor also generates medical emergency information during a medical emergency, and marks the medical emergency information according to the synchronization information.

In another embodiment, the invention is directed to a method in which audio is recorded during a medical emergency. Synchronization information is received from a medical device used during the medical emergency, and the recorded audio is marked according to the synchronization information.

The invention may provide a number of advantages. For example, use of an audio recorder to record audio during the medical emergency may allow a paramedic to generate a more accurate and complete run report for the medical emergency. Temporally correlating the recorded audio with the medical emergency by establishing synchronization with a medical device that generates medical emergency information, and providing a record for the medical emergency that includes recorded audio correlated with the medical emergency information, may increase the likelihood that an accurate and complete run report will be generated.

Audio recorder embodiments that record audio at selected times may be used to limit recording to periods of the medical emergency when useful information is likely to be recorded, such as at scene arrival and departure and when therapies are provided to a patient. By skipping portions of the medical emergency that are less likely to contain useful audio, audio recorder embodiments that selectively record audio may reduce the amount of time needed for a paramedic to generate a run report using the recorded audio. In some embodiments, the audio recorder may be configured to allow substantially hands-free use, freeing a user to treat a patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
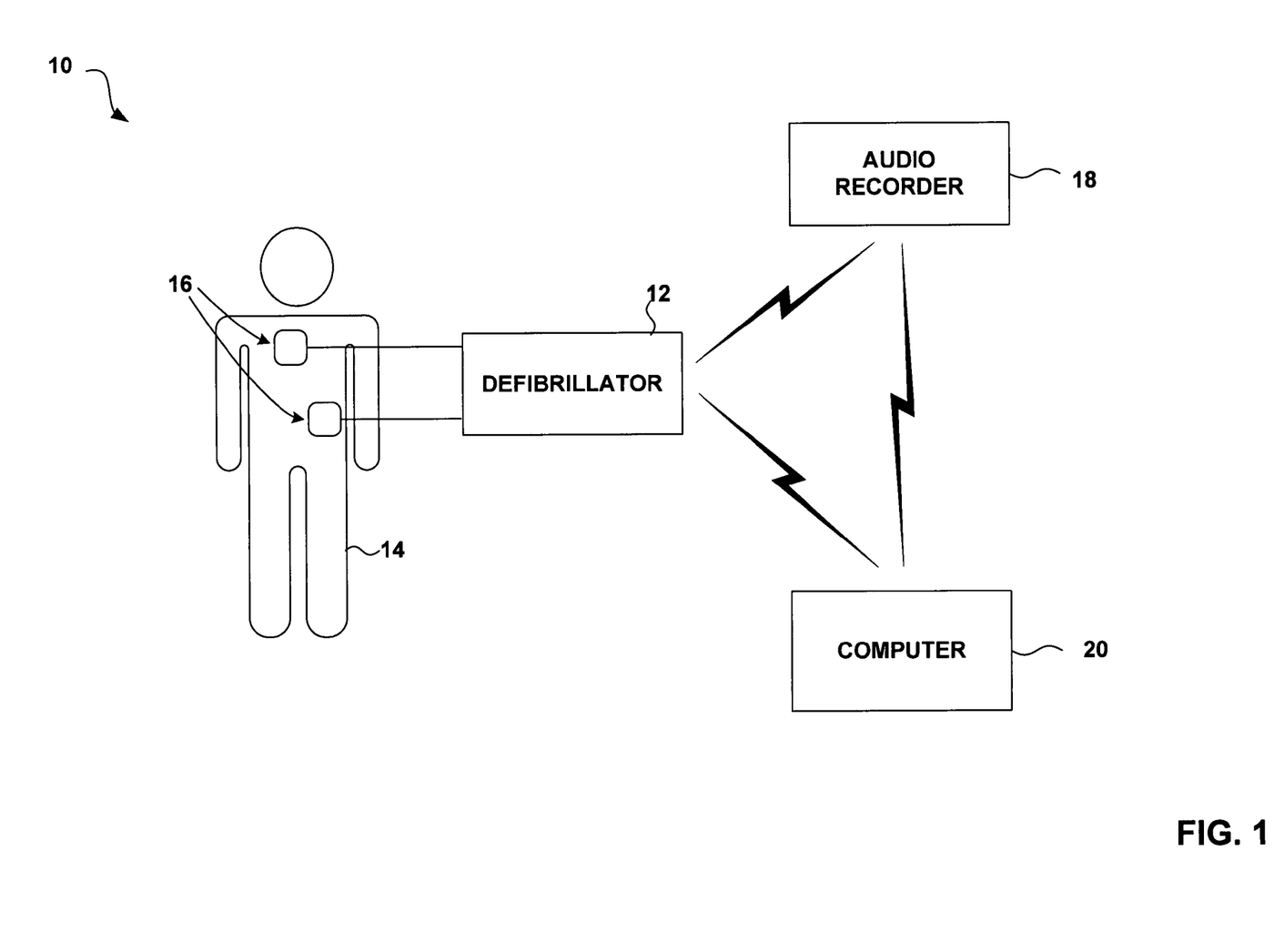
FIG. 1 is a block diagram illustrating an example system for managing audio recording during a medical emergency according to an embodiment of the invention.

FIG. 1 is a block diagram illustrating an example system 10 for managing audio recording during a medical emergency according to an embodiment of the invention. System 10 includes a defibrillator 12, shown in FIG. 1, coupled to a patient 14 via electrode set 16. A paramedic, for example, may use defibrillator 12 to treat patient 14 during the medical emergency. Defibrillator 12 may record medical emergency information during the medical emergency.

System 10 also includes an audio recorder 18. Audio recorder 18 may be used to record audio during the medical emergency. In some embodiments, audio recorder 18 may be used to selectively record audio at selected times during the medical emergency. As will be described in greater detail below, audio recorder 18 may selectively record audio in response to indications received from the paramedic and/or defibrillator 12.

Audio recorder 18 may be a portable digital audio recorder. Audio recorder 18 may be handheld. In some embodiments, audio recorder 18 may be worn by the paramedic, for example, on a wrist, arm or waist of the paramedic, to allow the hands of the paramedic to be free to treat patient 14. In some embodiments, where audio recorder 18 is used to selectively record audio at selected times, the paramedic may control recording by audio recorder 18 using voice commands for essentially hands-free operation. In some embodiments, audio recorder 18 may include a wired or wireless microphone located away from a housing of audio recorder 18 to more effectively record the voice of the paramedic, such as a microphone on a headset or clipped to a lapel.

Use of audio recorder 18 to record audio during the medical emergency may allow the paramedic to generate a more accurate and complete run report for the medical emergency. For example, the paramedic may record verbal descriptions of the scene, the condition of patient 14, vital signs of patient 14, a record of treatments provided to patient 14, and the like. Audio recorder 18 may also be used to record verbal responses of patient 14 to questions posed by the paramedic.

The paramedic may later review the audio recorded by audio recorder 18 during the medical emergency in order to generate a run report. Embodiments of audio recorder 18 that selectively record audio at selected times may be used to limit recording to periods of the medical emergency when useful information is likely to be recorded, such as at scene arrival and departure and when therapies are provided to patient 14. By skipping portions of the medical emergency that are less likely to contain useful audio, embodiments of audio recorder 18 that selectively record audio may reduce the amount of time needed for the paramedic to generate a run report using the recorded audio.

Audio recorder 18 generates correlation information to temporally correlate the recorded audio with the medical emergency. For example, audio recorder 18 may mark the recorded audio to correlate the recorded audio with the medical emergency. By generating correlation information, audio recorder 18 may, for example, allow the recorded audio to be more easily correlated with the medical emergency information recorded by defibrillator 12 during the medical emergency. This, in turn, may allow the paramedic to more easily and accurately generate a run report for the medical emergency.

As shown in FIG. 1, audio recorder 18 and defibrillator 12 may communicate via wired or wireless communication. Wireless communication between audio recorder 18 and defibrillator 12 may be by radio frequency communication. The radio frequency communication may be according to, for example, the 802.11 or Bluetooth specification sets.

As will be described in greater detail below, audio recorder 18 and defibrillator 12 may communicate via wireless communication in order to exchange synchronization information during the medical emergency. Audio recorder 18 may mark the recorded audio according to the synchronization information. Further, defibrillator 12 may mark the recorded medical emergency information according to the synchronization information. The exchange of synchronization information and marking according to the synchronization information may facilitate correlation of the recorded audio with the medical emergency information.

System 10 may also include a computer 20. Computer 20 may be, for example, a palmtop, laptop, or desktop computer. The paramedic may bring computer 20 to the scene of the medical emergency. For example, computer 20 could be carried by the paramedic or left in an ambulance. Alternatively, computer could be located at a dispatch center or hospital.

As shown in FIG. 1, computer 20 may communicate via wired or wireless communication with defibrillator 12 and audio recorder 18. Wireless communication between computer 20 and audio recorder 18 or defibrillator 12 may also be by radio frequency communication according to, for example, the 802.11 or Bluetooth specification sets.

Computer 20 may communicate with defibrillator 12 and audio recorder 18 in order to receive recorded medical emergency information from defibrillator 12, and recorded audio from audio recorder 18. Computer 20 may receive the recorded audio and medical emergency information at any time during or after the medical emergency, and need not obtain the recorded audio and medical emergency information at the same time.

As will be described in greater detail below, computer 20 may temporally correlate the recorded audio with the medical emergency information based on a synchronization scheme established between defibrillator 12 and audio recorder 18. Computer 20 may present a record for the medical emergency that includes the correlated recorded audio and medical emergency information to the paramedic. The record, with recorded audio and medical emergency information temporally correlated according to the synchronization scheme, may facilitate easier and more accurate run report generation by the paramedic.

Figure 2:
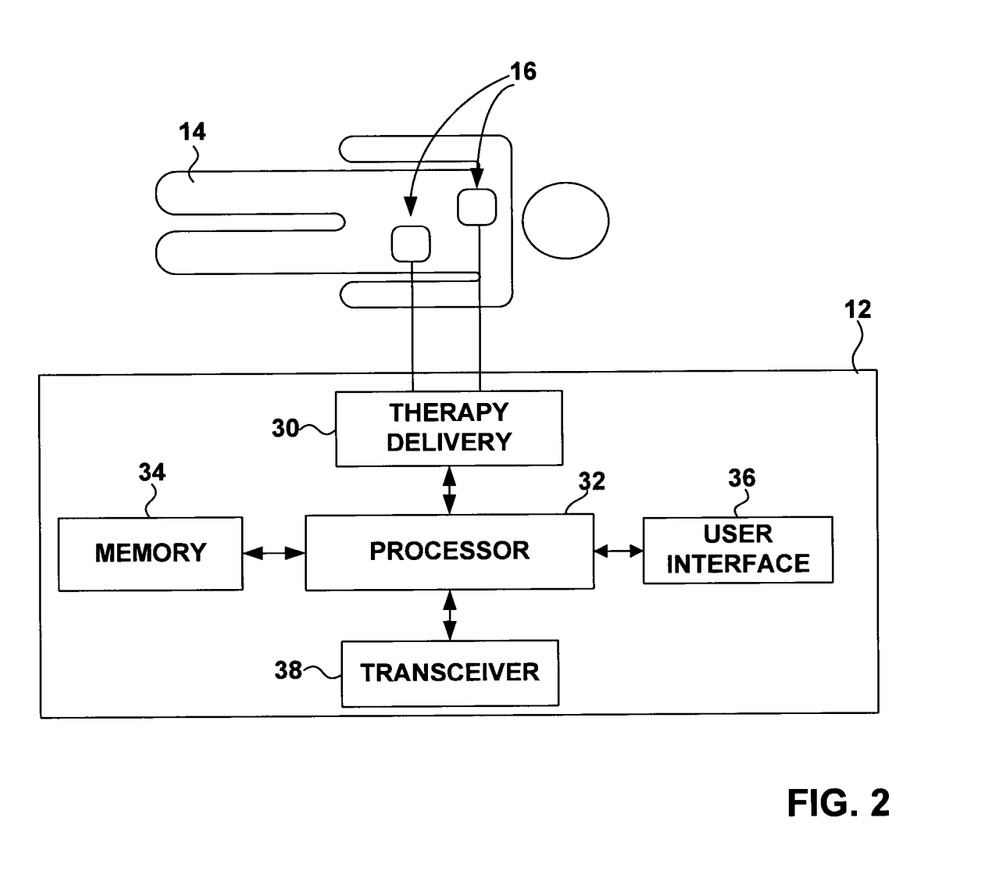
FIG. 2 is a block diagram illustrating an example defibrillator according to an embodiment of the invention.

FIG. 2 is a block diagram illustrating an example configuration of defibrillator 12 according to an embodiment of the invention. As mentioned above, defibrillator 12 is coupled to patient 14 via electrode set 16. Electrode set 16 may include hand-held electrode paddles or adhesive electrode pads placed on the skin of patient 14.

Electrode set 16 is coupled to a therapy delivery circuit 30 of defibrillator 12. Therapy delivery circuit 30 may include circuits for the delivery defibrillation pulses to patient 14 via electrode set 16. For example, therapy delivery circuit 30 may include an energy storage circuit, which may include capacitors, to store energy to deliver to patient 14 in the form of defibrillation pulses.

Therapy delivery circuit 30 may also include a switch that, when activated, couples the energy storage circuit to electrode set 16. Therapy delivery circuit 30 may also include circuits to filter or otherwise process signals received via electrode set 16 that represent the electrical activity of the heart of patient 14.

A processor 32 controls the operation of defibrillator 12 to monitor patient 14, provide therapy to patient 14, and generate medical emergency information during the treatment of patient 14. Specifically, processor 32 may control the delivery of therapy by therapy delivery circuit 30. Processor 32 may receive signals detected via electrode set 16, and monitor the electrical activity of the heart of patient 14.

Processor 32 may identify shockable rhythms, record an electrocardiogram (ECG), or record a heart rate over time. The ECG and heart rate may be stored in a memory 34 as medical emergency information for patient 14. Defibrillator 12 may also include additional sensors (not shown) coupled to processor 32, such as sensors to measure blood oxygen saturation, blood pressure, or respiration, and processor 32 may store the signals generated by these sensors as medical emergency information for patient 14.

Processor 32 may store an indication of the time of delivery of each defibrillation pulse delivered to patient 14 as medical emergency information within memory 34 for patient 14. Processor 32 may also store the energy level of each pulse and other characteristics of each pulse, such as the width, amplitude, or shape, as medical emergency information for patient 14. The paramedic may mark the time of the occurrence of various events, such as the delivery of drugs or the administration of cardiopulmonary resuscitation (CPR), during the treatment of patient 14 by, for example, pressing a key or button of a user interface 36 at the time when the event occurred. These event markers may also be included within medical emergency information for patient 14. Processor 32 may also display the ECG or other sensor data via a display of the user interface 36.

As will be described in greater detail below, processor 32 may exchange synchronization information with audio recorder 18 so that recorded medical emergency information may be correlated with an audio recording obtained by audio recorder 18. Processor 32 may also deliver recorded medical emergency information to computer 20 for generation of a record of the medical emergency that includes correlated medical emergency information and recorded audio. As illustrated in FIG. 2, defibrillator 12 may include a transceiver 38 for wireless communication with one or both of audio recorder 18 and computer 20.

Transceiver 38 may include an antenna to facilitate wireless communication via a radio frequency communication medium. Transceiver 38 may, for example, take the form of an integrated circuit or PCIMCA card with circuitry configured for wireless communication according, e.g., a wireless network interface card. The wireless network card may be compliant with one or more wireless communication standards such as to one or both of the Bluetooth or 802.11 specification sets. As an alternative, communication may be accomplished via wired connections, e.g., USB IEEE 1394 interfaces.

Processor 32 may, for example, take the form of a microprocessor, a digital signal processor (DSP), or an application specific integrated circuit (ASIC). Memory 34 may include program instructions that cause processor 32 to perform the functions attributed to defibrillator 12 herein. Memory 34 may include any of a variety of solid state, magnetic or optical media, such as RAM, ROM, CD-ROM, magnetic disk, or EEPROM.

Figure 3:
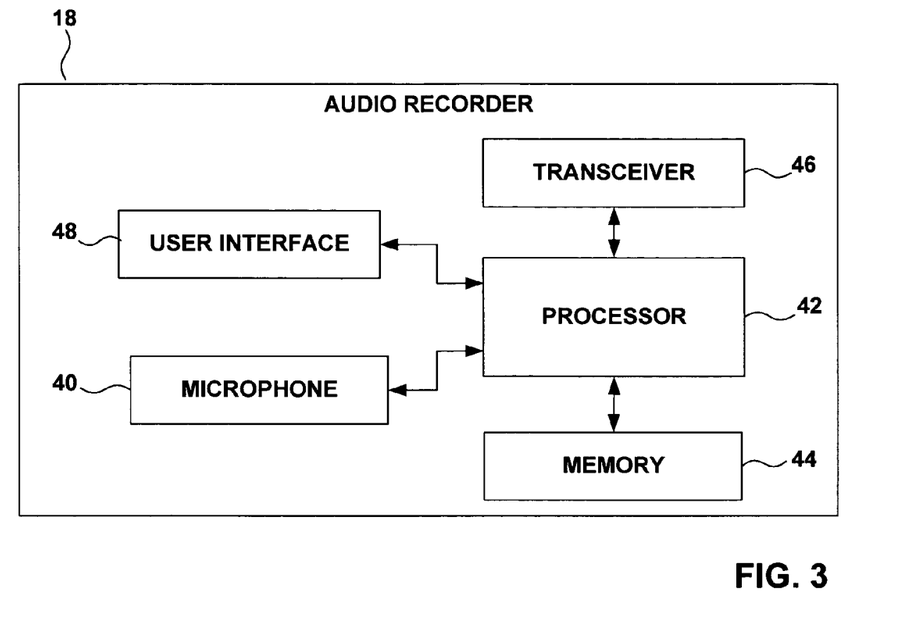
FIG. 3 is a block diagram illustrating an example audio recorder according to an embodiment of the invention.

FIG. 3 is a block diagram illustrating an example configuration of audio recorder 18 according to an embodiment of the invention. Audio recorder 18 includes a microphone 40 to detect sound, which as described above may be integral with audio recorder 18, or located outside a housing of audio recorder 18. Microphone 40 is coupled to a processor 42, which receives audio detected by microphone 40, and stores the audio in a memory 44.

As will be described in greater detail below, processor 42 may exchange synchronization information with defibrillator so that recorded audio may be correlated with medical emergency information generated by defibrillator 12. Processor 42 may also deliver recorded audio to computer 20 for generation of a record of the medical emergency that includes correlated medical emergency information and recorded audio. As illustrated in FIG. 3, audio recorder 18 may include a transceiver 46 for wireless communication with one or both of defibrillator 12 and computer 20.

Transceiver 46 may include an antenna to facilitate wireless communication via a radio frequency communication medium. Transceiver 46 may, for example, take the form of an integrated circuit or PCIMCA card with circuitry configured for wireless communication according, e.g., a wireless network interface card. The wireless network card may be compliant with one or more wireless communication standards such as to one or both of the Bluetooth or 802.11 specification sets. Again, as an alternative, communication may be accomplished via a wired link.

In embodiments where audio recorder 18 selectively records audio, processor 42 may receive record indications from the paramedic via a user interface 48, which may include various buttons. In some embodiments, processor 42 may interpret audio signals received via microphone, and record audio in response to recognition of a voice command. In other embodiments, processor 42 may record in response to indications received from defibrillator 12 via transceiver 46.

Processor 42 may, for example, take the form of a microprocessor, a digital signal processor (DSP), or an application specific integrated circuit (ASIC). Memory 44 may include program instructions that cause processor 42 to perform the functions attributed to audio recorder 18 herein. Memory 44 may include any of a variety of solid state, magnetic or optical media, such as RAM, ROM, CD-ROM, magnetic disk, or EEPROM.

Figure 4:
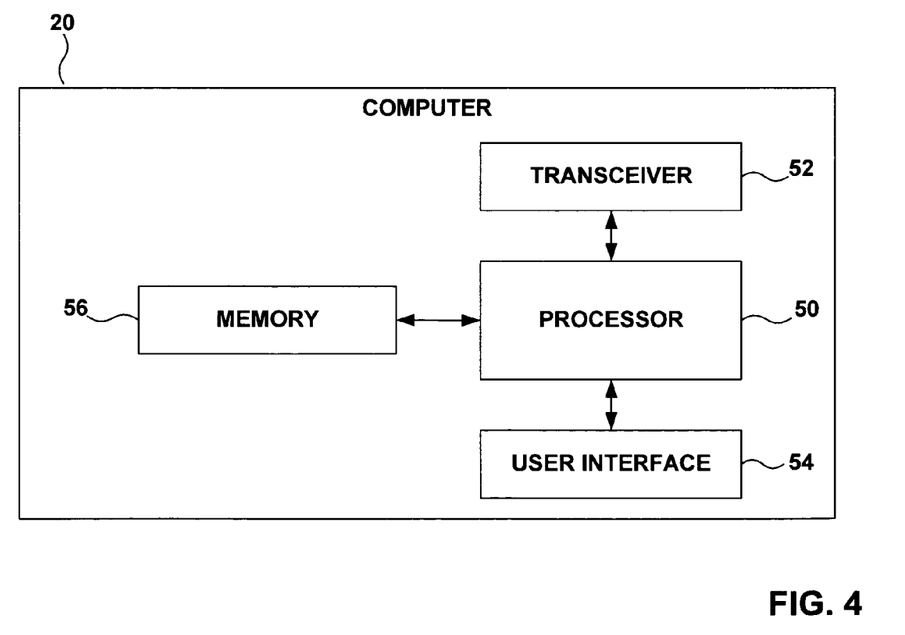
FIG. 4 is a block diagram illustrating an example computer according to an embodiment of the invention.

FIG. 4 is a block diagram illustrating an example configuration of computer 20 according to an embodiment of the invention. Computer 20 includes a processor 50, which may receive recorded audio from audio recorder 18 and medical emergency information from defibrillator 12. Processor 50 may wirelessly communicate with audio recorder 18 and defibrillator 12 via a transceiver 52 in order to receive recorded audio and medical emergency information.

As will be described in greater detail below, processor 50 may generate a record of the medical emergency that includes the medical emergency information and correlated audio recording. Processor 50 may present this record via a user interface 66, which may include a display, such as a CRT, LED, or LCD display, a speaker, and user input devices, such as a keypad or pointing device. Processor 50 may present a graphical user interface (GUI) via user interface 66. The paramedic may interact with the GUI in order to review the generated record for the medical emergency.

Processor 50 may, for example, take the form of a microprocessor, a digital signal processor (DSP), or an application specific integrated circuit (ASIC). A memory 56 may include program instructions that cause processor 50 to perform the functions attributed to computer 20 herein. Memory 56 may include any of a variety of solid state, magnetic or optical media, such as RAM, ROM, CD-ROM, magnetic disk, or EEPROM.

Figure 5:
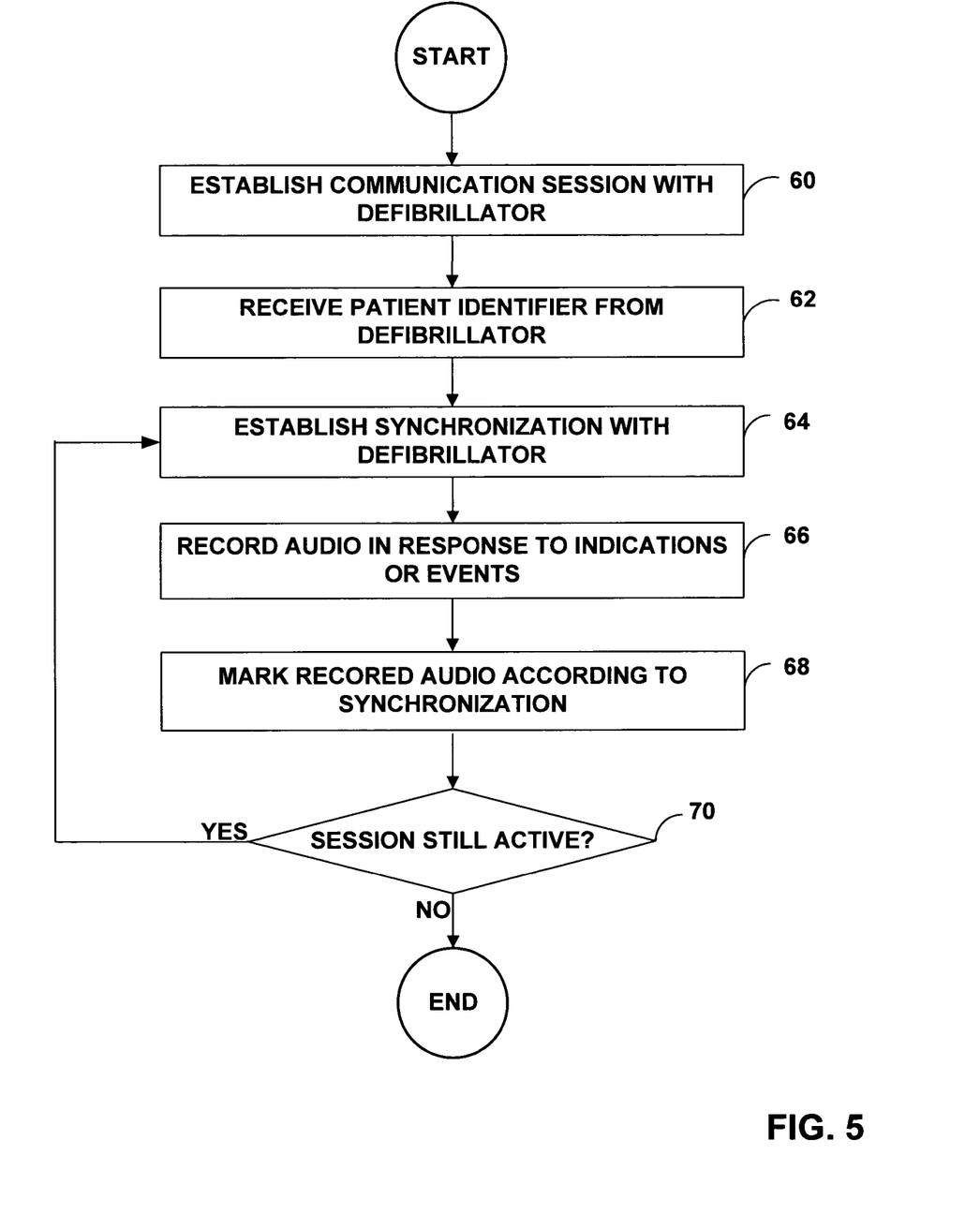
FIG. 5 is a flow diagram illustrating an example method that may be employed by an audio recorder to record audio during a medical emergency according to an embodiment of the invention.

FIG. 5 is a flow diagram illustrating an example method that may be employed by audio recorder 18 to record audio during a medical emergency according to an embodiment of the invention. Specifically, FIG. 5 illustrates a method in which audio recorder 18 selectively records audio, and marks the recorded audio according to synchronization information received from defibrillator 12. Audio recorder 18 and defibrillator 12 may establish a communication session (60), and audio recorder 18 may receive the synchronization information via the communication session. As mentioned above, the communication session may be a wireless communication session according to, for example, the 802.11 or Bluetooth specification sets. Alternatively, communication may be via a wired connection.

Audio recorder 18 and defibrillator 12 may establish the communication session at any time when they are both turned on. For example, the communication session may be established when the paramedic arrives at the scene of the medical emergency, or while the paramedic is en route to the medical emergency. Further, audio recorder 18 may record audio and defibrillator 12 may generate medical emergency information before, as well as after the communication session is established.

Audio recorder 18 may receive a patient identifier for patient 14 from defibrillator 12 (62). Defibrillator 12 may assign a unique identifier to each patient treated by defibrillator, and mark medical emergency information generated for each patient with the assigned identifier to allow later retrieval of medical emergency information for a particular patient. Audio recorder 18 may mark audio recorded during the medical emergency involving patient 14 with the received patient identifier so that the recorded audio for patient 14 may be correctly matched to the medical emergency information for patient 14.

Audio recorder 18 and defibrillator 12 may establish a synchronization scheme. (64). Audio recorder 18 may selectively record audio in response to record indications received from the paramedic, or event indications received from defibrillator 12 (66). Audio recorder 18 marks the recorded audio according to the synchronization scheme, so that recorded audio may be correlated with generated medical emergency information (68). Audio recorder 18 continues to record audio and mark the recorded audio so long as the communication session is active (70).

In some embodiments, audio recorder 18 and defibrillator 12 may synchronize their respective clocks. For example, audio recorder 18 may receive periodic synchronization messages or packets from defibrillator 12, and adjust a clock maintained by audio recorder 18 based on the message or packet. Defibrillator 12 may mark generated medical emergency information according to the clock maintained by defibrillator 12, and audio recorder 18 may mark recorded audio according to the synchronized clock maintained by audio recorder 18. Time stamps used to mark medical emergency information and recorded audio may be of sufficient resolution such that synchronization error caused by the amount of time required to transmit and process synchronization messages or packets will generally not lead to errors when correlating the medical emergency information and recorded audio.

In some embodiments, audio recorder 18 and defibrillator 12 may establish synchronization based on events that occur during the medical emergency. When a medical event occurs, such as delivery of a therapy, defibrillator 12 may a send an event identifier message to audio recorder 12. Defibrillator 12 may mark medical emergency information with the medical event identifier, and audio recorder 18 may mark recorded audio with the medical event identifier. The medical event identifier may be used to correlate the recorded audio with the appropriate portions of the medical emergency information.

As mentioned above, audio recorder 18 may selectively record audio in response to receiving event indications from defibrillator 12. In embodiments where audio recorder 18 receives event identifiers from defibrillator 12, audio recorder 18 may record audio in response to receiving an event identifier, and mark the recorded audio with the event identifier. In embodiments where audio recorder 18 selectively records audio in response to receiving a record indication from the paramedic, audio recorder 18 may send a recording event identifier to defibrillator 12, and mark the recorded audio with the recording event identifier. Defibrillator 12 may mark the medical emergency information with the recording event identifier so that the recorded audio may be correlated with the appropriate portion of the medical emergency information.

In embodiments where audio recorder 18 selectively records audio, the length of time that audio recorder 18 records after receiving an indication may be determined in a number of ways. For example, audio recorder 18 may continuously record while a button of user interface 48 is depressed, or record for a fixed interval after the button is depressed or a voice command is received via microphone 40. Different buttons or commands may be used for different lengths of time. As another example, audio recorder may continuously record after a button is depressed or a voice command is received so long as the volume of the sound being recorded exceeds a threshold.

In embodiments where audio recorder 18 receives event indications, audio recorder 18 may also determine the length of time to record based on type of event. For example, a longer record period may be useful at the start of the synchronization session, e.g., defibrillator power-up, to capture a description of the scene and the condition of patient 14. The length of a record period may be configured by the paramedic.

Figure 6:
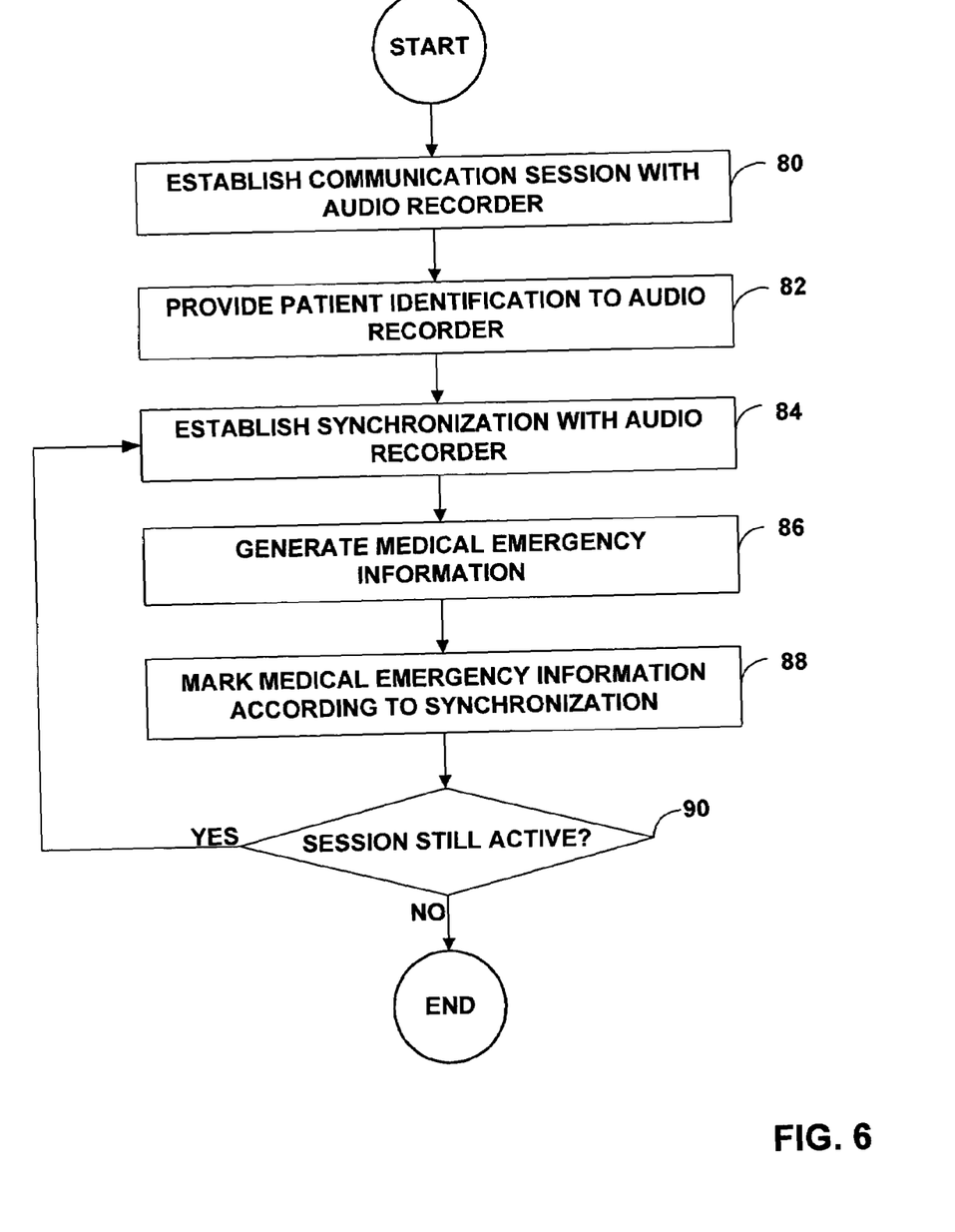
FIG. 6 is a flow diagram illustrating an example method that may be employed by a medical device to generate medical emergency information during a medical emergency according to an embodiment of the invention.

FIG. 6 is a flow diagram illustrating an example method that may be employed by defibrillator 12 to generate medical emergency information during a medical emergency according to an embodiment of the invention. Specifically, FIG. 6 illustrates a method in which defibrillator 12 generates medical emergency information, and marks the medical emergency information according to a synchronization established with audio recorder 18. In order to establish synchronization, defibrillator 12 and audio recorder 18 may establish a communication session as described above with reference to FIG. 5 (80).

Defibrillator 12 may provide a patient identifier to audio recorder 18 (82), and establish a synchronization scheme with audio recorder 18 (84) as described above with reference to FIG. 5. For example, defibrillator 12 may provide clock synchronization messages and/or medical event identifiers to audio recorder 18, as described above. Defibrillator 12 may also receive recording event identifiers from audio recorder 18, as described above.

As defibrillator 12 generates medical emergency information (86), defibrillator 12 may mark the medical emergency information according to the synchronization scheme (88) so that audio recorded by audio recorder 18 may be correlated with the medical emergency information. For example, defibrillator 12 may mark the medical emergency information with time-stamps or identifiers. Defibrillator 12 may mark maintain synchronization and mark medical emergency information so long as the communication session is active (90).

Figure 7:
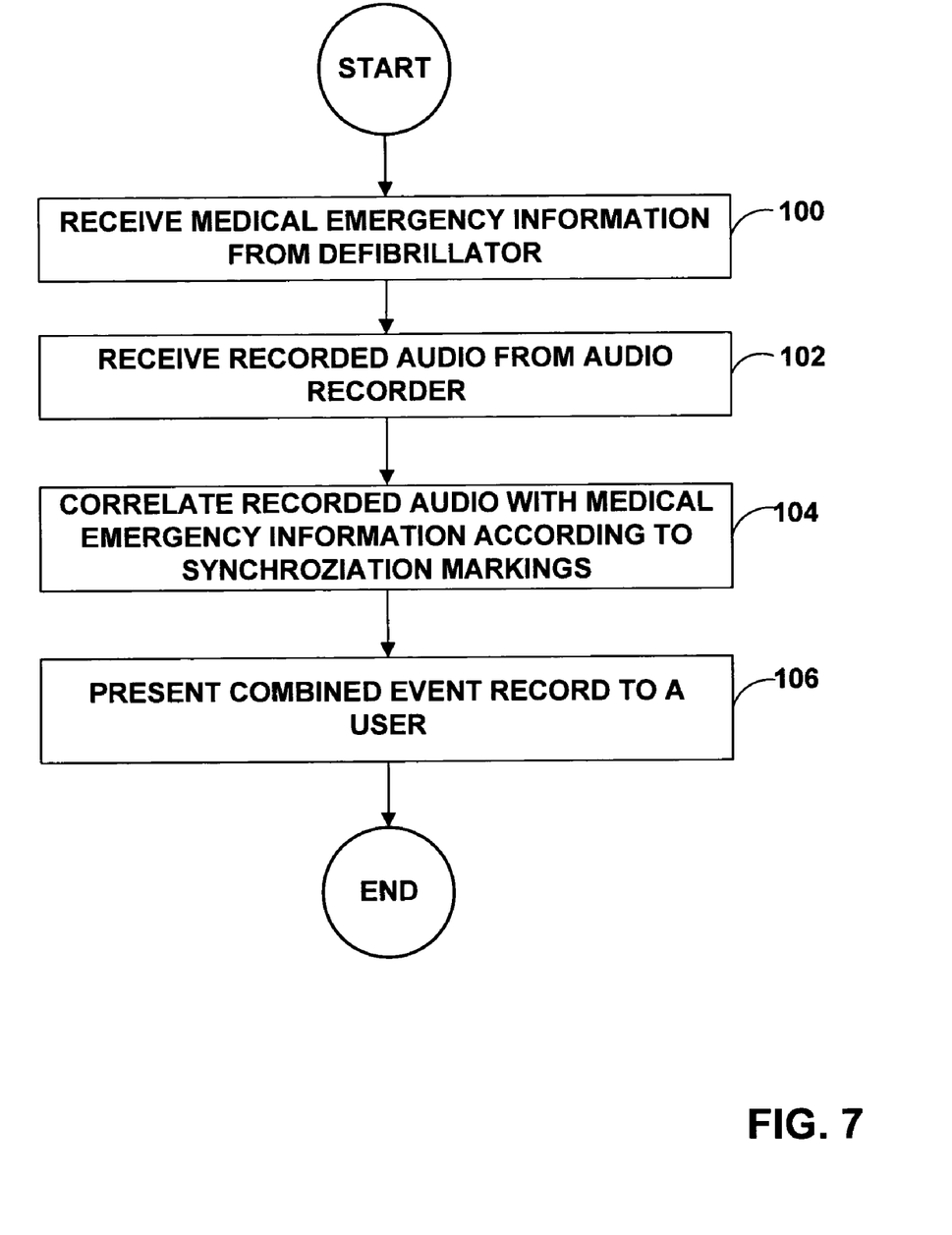
FIG. 7 is a flow diagram illustrating an example method that may be employed by a computer to present recorded audio and medical emergency information to a user according to an embodiment of the invention.

FIG. 7 is a flow diagram illustrating an example method that may be employed by computer 20 to present recorded audio and medical emergency information to the paramedic according to an embodiment of the invention. Computer 20 receives medical emergency information generated by defibrillator 12 for the medical emergency involving patient 14 (100), and audio recorded by audio recorder 18 during the medical emergency (102). As described above, computer 20 may wirelessly communicate with defibrillator 12 and audio recorder 18 at any times during or after the medical emergency in order to receive the medical emergency information and recorded audio.

Computer 20 correlates the recorded audio with the medical emergency information according to the synchronization markings within each of the recorded audio and medical emergency information (104) in order to create a combined event record for the medical emergency involving patient 14. Computer 20 may match recorded audio with the correct medical emergency information based on a patient identifier, and may correlate the recorded audio with the medical emergency information by linking the recorded audio to appropriate portions of the medical emergency information based on the synchronization markings. Computer 20 may present the combined medical event record to the paramedic via a GUI, as will be described in greater detail below.

Figure 8:
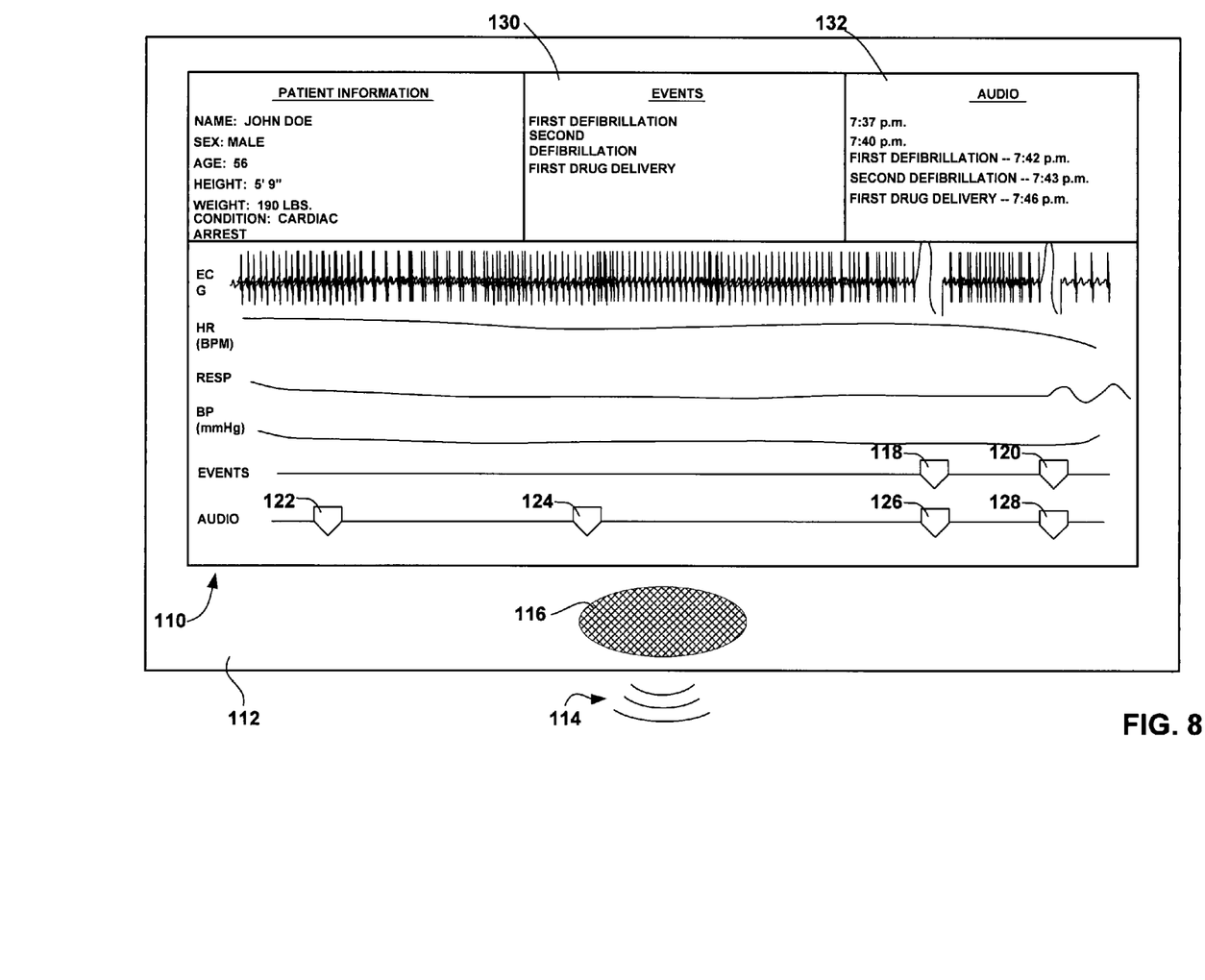
FIG. 8 is a diagram illustrating an example graphical user interface that may be employed by a computer to present audio recordings and medical emergency information to a user according to an embodiment of the invention.

FIG. 8 is a diagram illustrating an example GUI 110 that may be employed by computer 20 to present recorded audio and medical emergency information to a user as a combined event record for a medical emergency. GUI 110 may be provided via a display 112 of user interface 54 of computer 20. Recorded audio 114 may be played back via a speaker 116 of user interface 54.

As shown in FIG. 8, GUI 110 may display some of the medical emergency information as waveforms. GUI 110 may allow for playback of the medical emergency information at varying speeds, pausing, and the like. GUI may also display numerical values associated with some of the waveforms, e.g. heart rates or blood pressures, and display the time at which the numerical values were recorded according to the clock maintained by defibrillator 12.

As shown in FIG. 8, GUI 110 may display icons 118 and 120 that indicate the time at which medical events, such as the delivery of therapy, occurred during the medical emergency. GUI 110 may also display icons 122–128 that indicate the time at which audio was recorded during the medical emergency. Computer 20 may determine the positions of icons 122–128 relative to the medical emergency information based on the synchronization markings within each of the recorded audio and medical emergency information.

A user may play back the medical emergency information, and computer 20 may play the selectively recorded audio at the appropriate times relative to the medical emergency information as determined based on the synchronization markings. The user may also select a particular portion of the medical emergency information and recorded audio for playback by selecting one of icons 120–128. GUI 110 may also display lists 130 and 132 to allow a user to select a particular portion of the medical emergency information and recorded audio for playback. Various embodiments of the invention have been described. However, one skilled in the art will appreciate that various modifications may be made to the described embodiments without departing from the scope of the invention. For example, although medical emergency information has been described herein as generated by a defibrillator, medical emergency information may be generated by any medical device used to treat a patient during a medical emergency. A drug delivery pump or a blood pressure monitor may generate medical emergency information, for example. An audio recorder may communicate with any such medical device to establish synchronization, and may communicate with multiple devices during a single medical emergency. Moreover, multiple audio recorders may be used for a single medical emergency. A computer may combine medical emergency information collected by multiple medical devices with audio recorded by multiple audio recorders.

Further, the invention is not limited to use by paramedics. It is believed that the invention may be used to manage the recording of audio during medical emergencies in a number of environments. As one example, the invention may be used in a hospital emergency room environment. Moreover, multiple users may interact with different components of a system according to the invention. For example, a first user may record audio during the medical emergency, while other users monitor and provide therapy to a patient using one or more medical devices. Yet another user may use a computer to review a combined record for the medical emergency that includes recorded audio correlated with medical emergency information.

Although audio recorders and medical devices have been described as communicating via RF communication, the communication may be via infrared or wired communication, e.g., via a data cable. Likewise, communication between a computer and an audio recorder or medical device may be via infrared or wired communication. Computer may also receive recorded audio or medical emergency information that is stored on a removable medium, such as a data card. Further recorded audio and medical emergency information may be received from a single source, such as when one of an audio recorder or medical device first receives the information collected by the other before the computer retrieves the information.

Further, an audio recorder, medical device, and computer need not be embodied as separate devices. A single device may include a combined audio and medical device, a combined audio recorder and computer, a combined medical device and computer, or a combined audio recorder, medical device, and computer. These and other embodiments are within the scope of the following claims.

The invention claimed is:

1. A method comprising:
 recording audio during a medical emergency;
 receiving synchronization information from a separate medical device that at least one of treats or physiologically monitors a patient during the medical emergency; and
 marking the recorded audio according to the synchronization information to temporally correlate the recorded audio with the medical emergency.

2. The method of claim 1, in which receiving synchronization information comprises receiving clock information from the medical device, and marking the recorded audio comprises marking the recorded audio with a time.

3. The method of claim 1, in which receiving synchronization information comprises receiving a treatment event identifier from the medical device, and marking the recorded audio comprises marking the recorded audio with the treatment event identifier.

4. The method of claim 1, in which receiving synchronization information comprises:
 establishing a local wireless communication session with the medical device; and
 receiving the synchronization information via the wireless communication session.

5. The method of claim 1, in which the medical device includes a defibrillator.

6. The method of claim 1, further comprising:
 communicating a recording event identifier to the medical device; and
 marking the recorded audio with the recording event identifier.

7. The method of claim 1, further comprising:
 receiving a patient identifier from the medical device; and
 marking the recorded audio with the patient identifier.

8. The method of claim 1, in which marking the recorded audio comprises marking the recorded audio to temporally correlate the audio with medical emergency information generated by the medical device, wherein the method further includes providing the marked recorded audio to a device for generation of a record of the medical emergency that includes temporally correlated medical emergency information and recorded audio.

9. The method of claim 8, in which the medical emergency information includes at least one of an electrocardiogram, a capnograph, a plethysmograph, a heart rate over time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

10. The method of claim 1, in which recording audio during a medical emergency comprises selectively recording audio at selected times during the medical emergency.

11. The method of claim 10, in which selectively recording audio comprises:
 receiving a record indication from a user; and
 recording audio in response to receiving the indication.

12. The method of claim 10, in which selectively recording audio comprises:
 receiving a treatment event indication from the medical device; and
 recording audio in response to receiving the indication.

13. The method of claim 12, further comprising:
 identifying an event type based on the treatment event indication; and
 determining a length of time to record based on the event type.

14. The method of claim 12, in which recording audio comprises receiving an indication of a length of time to record from the medical device.

15. A device comprising:
 a microphone to detect sound;
 a receiver; and
 a processor coupled to the microphone and the receiver, wherein the processor records audio detected by the microphone during a medical emergency, receives synchronization information via the receiver from a separate medical device that at least one of treats or physiologically monitors a patient during the medical emergency, and marks the recorded audio according to the synchronization information to temporally correlate the recorded audio with the medical emergency.

16. The device of claim 15, in which the processor receives clock information from the medical device via the receiver and marks the recorded audio with a time.

17. The device of claim 15, in which the processor receives a treatment event identifier from the medical device and marks the recorded audio with the treatment event identifier.

18. The device of claim 15, in which the receiver comprises a transceiver, and the processor establishes a local wireless communication session with the medical device via the transceiver and receives synchronization information via the communication session.

19. The device of claim 15, in which the medical device includes a defibrillator.

20. The device of claim 15, further comprising a transmitter, wherein the processor transmits a recording event identifier to the medical device and marks the recorded audio with the recording event identifier.

21. The device of claim 15, wherein the processor receives a patient identifier from the medical device via the receiver and marks the recorded audio with the patient identifier.

22. The device of claim 15, in which the processor marks the recorded audio to temporally correlate the audio with medical emergency information generated by the medical device, and provides the marked recorded audio to another device for generation of a record of the medical emergency that includes temporally correlated medical emergency information and recorded audio.

23. The device of claim 22, in which the medical emergency information includes at least one of an electrocardiogram, a capnograph, a plethysmograph, a heart rate over time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

24. The device of claim 15, in which the processor selectively records audio at selected times during the medical emergency.

25. The device of claim 24, further comprising a user interface, wherein the processor selectively records audio in response to receiving a record indication from a user via the user interface.

26. The device of claim 24, in which the processor selectively records audio in response to receiving a treatment event indication from a medical device used during the medical emergency.

27. The device of claim 26, in which the processor identifies an event type based on the treatment event indication, and determines a length of time to record based on the event type.

28. The device of claim 26, in which the processor receives an indication of a length of time to record from the medical device.

29. The device of claim 15, in which the device comprises a portable audio recorder.

30. The device of claim 29, in which the device is configured to be worn by a user.

31. A method comprising:
receiving medical emergency information from a medical device used during a medical emergency; and
correlating recorded audio obtained by an audio recorder during the medical emergency with the medical emergency information based on a synchronization scheme established between the medical device and the audio recorder.

32. The method of claim 31, further comprising presenting a record of the medical emergency that includes the correlated medical emergency information and recorded audio to a user.

33. The method of claim 32, in which presenting a record comprises:
playing a selected portion of the recorded audio; and
displaying a portion of the medical emergency information associated with the selected portion of the recorded audio.

34. The method of claim 33, further comprising:
presenting a list of different portions of the recorded audio; and
receiving user input identifying the selected portion of the recorded audio.

35. The method of claim 31, in which the medical emergency information includes at least one of an electrocardiogram, a capnograph, a plethysmograph, a heart rate over time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

36. The method of claim 31, in which the medical device includes a defibrillator.

37. A device comprising:
a receiver to receive information from a medical device used during a medical emergency; and
a processor to receive medical emergency information from the medical device via the receiver and correlate recorded audio obtained by an audio recorder during the medical emergency with the medical emergency information based on a synchronization scheme established between the medical device and the audio recorder.

38. The device of claim 37, further comprising a user interface, wherein the processor presents a record of the medical emergency that includes the correlated medical emergency information and recorded audio to a user via the user interface.

39. The device of claim 38, in which the processor plays a selected portion of the recorded audio, and displays a portion of the medical emergency information associated with the selected portion of the recorded audio.

40. The device of claim 39, in which the processor presents a list of different portions of the recorded audio, and receives user input identifying the selected portion of the recorded audio.

41. The device of claim 37, in which the medical emergency information includes at least one of an electrocardiogram, a capnograph, a plethysmograph, a heart rate over time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

42. The device of claim 37, in which the medical device includes a defibrillator.

43. A computer-readable medium comprising instructions that cause a processor to:
receive medical emergency information from a medical device used during a medical emergency; and
correlate recorded audio obtained by an audio recorder during the medical emergency with the medical emergency information based on a synchronization scheme established between the medical device and the audio recorder.

44. The computer-readable medium of claim 43, further comprising instructions that cause a processor to present a record of the medical emergency that includes the correlated medical emergency information and recorded audio to a user.

45. The computer-readable medium of claim 44, in which the instructions cause a processor to:
play a selected portion of the recorded audio; and
display a portion of the medical emergency information associated with the selected portion of the recorded audio.

46. The computer-readable medium of claim 45, in which the instructions cause a processor to:
present a list of different portions of the recorded audio; and
receive user input identifying the selected portion of the recorded audio.

47. A method comprising:
providing synchronization information to an audio recorder;
generating medical emergency information during a medical emergency; and
marking the medical emergency information according to the synchronization information.

48. The method of claim 47, in which providing synchronization information comprises providing clock information to the audio recorder, and marking the medical emergency information comprises marking the medical emergency information with a time.

49. The method of claim 47, in which providing synchronization information comprises providing a treatment event identifier to the audio recorder, and marking medical emergency information comprises marking the recorded audio with the treatment event identifier.

50. The method of claim 47, in which providing synchronization information to an audio recorder comprises:
establishing a local wireless communication session with the audio recorder; and
providing the synchronization information to the audio recorder via the communication session.

51. The method of claim 47, further comprising:
receiving a recording event identifier from the audio recorder; and
marking the medical emergency information with the recording event identifier.

52. The method of claim 47, further comprising:
providing a patient identifier to the audio recorder; and
marking the medical emergency information with the patient identifier.

53. The method of claim 47, in which the medical emergency information includes at least one of an electrocardiogram, a capnograph, a plethysmograph, a heart rate over time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

54. A device comprising:
a transmitter to provide information to an audio recorder; and
a processor to provide synchronization information to the audio recorder via the transmitter, generate medical emergency information during a medical emergency, and mark the medical emergency information according to the synchronization information.

55. The device of claim 54, in which the processor provides clock information to the audio recorder, and marks the medical emergency information with a time.

56. The device of claim 54, in which the processor provides a treatment event identifier to the audio recorder, and marks the medical emergency information with the treatment event identifier.

57. The device of claim 54, in which the transmitter comprises a transceiver, wherein the processor establishes a local wireless communication session with the audio recorder via the transceiver and provides synchronization information to the audio recorder via the communications session.

58. The device of claim 54, in which the transmitter comprises a transceiver, and the processor receives a recording event identifier from the audio recorder via the transceiver and marks the medical emergency information with the recording event identifier.

59. The device of claim 54, in which the processor provides a patient identifier to the audio recorder, and marks the medical emergency information with the patient identifier.

60. The device of claim 54, in which the processor marks the medical emergency information to temporally correlate the medical emergency information audio recorded by the audio recorder, and provides the marked medical emergency information to another device for generation of a record of the medical emergency that includes temporally correlated medical emergency information and recorded audio.

61. The device of claim 54, in which the medical emergency information includes at least one of an electrocardiogram, a capnograph, a plethysmograph, a heart rate aver time, a pulse rate over time, a blood oxygen saturation over time, a blood pressure over time, end tidal carbon dioxide measurements, measurements of the fraction of carbon dioxide in air inspired or expired, one or more therapies delivered to a patient, and times at which the one or more therapies were delivered to the patient.

62. The device of claim 54, in which the processor provides an indication of a length of time to record to the audio recorder.

63. The device of claim 54, in which the device comprises a defibrillator.

64. A method comprising:
recording audio during a medical emergency; and
receiving synchronization information from a separate medical device that at least one of treats and monitors a patient during the medical emergency; and
marking the recorded audio according to the synchronization information.

65. The method of claim 64, wherein marking the recorded audio comprises marking the recorded audio to temporally correlate the recorded audio with the medical emergency.

66. The method of claim 64, in which receiving synchronization information comprises receiving clock information from the medical device, and marking the recorded audio comprises marking the recorded audio with a time.

67. The method of claim 64, in which receiving synchronization information comprises receiving a treatment event identifier from the medical device, and marking the recorded audio comprises marking the recorded audio with the treatment event identifier.

68. The method of claim 64, in which recording audio during a medical emergency comprises selectively recording audio at selected times during the medical emergency.

69. A system comprising:
a medical device that includes a first housing, and that at least one of treats or physiologically monitors a patient during a medical emergency; and
a portable audio recorder that includes a second housing, records audio during a medical emergency, receives synchronization information from the medical device, and marks the recorded audio according to the synchronization information to temporally correlate the recorded audio with the medical emergency.

70. The system of claim 69, wherein the medical device and the portable audio recorder establish a local wireless communication session, and the portable audio recorder receives the synchronization information via the local wireless communication session.

71. The system of claim 69,
wherein the medical device generates medical emergency information during the medical emergency, and marks the medical emergency information according to the synchronization information,
the system further comprising a computer that receives the marked recorded audio from the audio recorder and the marked medical emergency information from the medical device, temporally correlates the medical emergency information and the recorded audio according to the marking of the medical emergency information and the recorded audio, and generates a record of the medical emergency that includes the temporally correlated medical emergency information and recorded audio.

72. The system of claim 69, in which the medical device comprises an external defibrillator, and the audio recorder is configured to be worn by a user.

* * * * *